United States Patent [19]

Weinstock

[11] 4,251,525
[45] Feb. 17, 1981

[54] 3-ALLYL-7,8-DIHYDROXY-6-HALO-1-(4-HYDROXYPHENYL)-2,3,4,5-TETRAHYDRO-1H-3-BENZAZEPINE DERIVATIVES

[75] Inventor: Joseph Weinstock, Phoenixville, Pa.

[73] Assignee: SmithKline Corporation, Philadelphia, Pa.

[21] Appl. No.: 42,680

[22] Filed: May 25, 1979

Related U.S. Application Data

[63] Continuation-in-part of Ser. No. 742,965, Nov. 17, 1976, Pat. No. 4,180,765.

[51] Int. Cl.³ .................... A61K 31/55; C07D 223/16
[52] U.S. Cl. ............................. 424/244; 260/239 BB
[58] Field of Search ................ 260/239 BB; 424/244

Primary Examiner—Jose Tovar
Assistant Examiner—D. B. Springer
Attorney, Agent, or Firm—William H. Edgerton; Richard D. Foggio; Alan D. Lourie

[57] ABSTRACT

3-Allyl-7,8-dihydroxy-6-halo-1-(4-hydroxyphenyl)-2,3,4,5-tetrahydro-1H-3-benzazepine derivatives are prepared by N-allylation of 7,8-dimethoxy-6-halo-1-(4-methoxyphenyl)-2,3,4,5-tetrahydro-1H-3-benzazepine using an allyl halide in acetonitrile in the presence of base followed by O-demethylation. These compounds have a unique cardiovascular effect in that they are potent renal vasodilators and also induce bradycardia.

7 Claims, No Drawings

3-ALLYL-7,8-DIHYDROXY-6-HALO-1-(4-HYDROXYPHENYL)-2,3,4,5-TETRAHYDRO-1H-3-BENZAZEPINE DERIVATIVES

This application is a continuation-in-part application of copending Ser. No. 742,965 filed Nov. 17, 1976, now U.S. Pat. No. 4,180,765, issued July 10, 1979.

This invention concerns a group of compounds whose structures have a 1-phenyl-2,3,4,5-tetrahydro-1H-3-benzazepine skeleton which specifically has a 6-halo-7,8-dihydroxy substitution pattern in the benz-ring, an allyl attached to the N-ring member at position 3 and a hydroxy substituent on the 1-phenyl. These compounds are renal vasodilators with a novel bradycardic effect. As such they are of particular interest for treating angina pectoris.

Statement of the Prior Art

Scherico Swiss Pat. No. 555,831 discloses a generic group from which all the necessary structural parameters discussed herein may be selected by hindsight. Certain isolated species are mentioned in this reference which have one of these necessary parameters such as the N-allyl group. Mull, U.S. Pat. No. 3,496,166 is an even broader generic reference than is Scherico but discloses no N-allyl containing species. Kaiser et al., U.S. Pat. No. 4,011,319 and U.S. Pat. No. 4,052,506, disclose 1-phenyl-2,3,4,5-tetrahydro-1H-3-benzazepine derivatives having a single structural parameter of the compounds of this invention. The first of these discloses also general renal vasodilator activity for the compounds disclosed therein. Mull, U.S. Pat. No. 3,609,138 is a very broad generic reference similar to the Scherico patent but with no N-allyl containing species disclosed. None of these references disclose any utility for the compounds therein as antianginal agents. Nor is the pharmacological spectrum described herein anticipated by the prior art.

Certain overseas counterparts of my parent application mentioned above have issued such as Belgian Pat. No. 860,774, published May 16, 1978. These are not admitted to be prior art against this inventon.

Description of the Invention

The compounds of this invention are represented by the following structural formula:

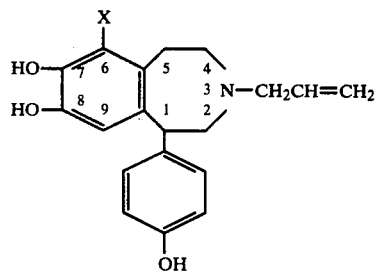

I in which X is halo, that is fluoro, chloro, bromo or iodo.

The pharmaceutically acceptable acid addition salts having the utility of the free bases of Formula I, prepared by methods well known to the art, are formed with both inorganic or organic acids, for example: maleic, fumaric, benzoic, ascorbic, pamoic, succinic, bis-methylenesalicylic, methanesulfonic ethanedisulfonic, acetic, oxalic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids. The hydrohalic and especially methanesulfonic acid salts are of particular utility because of good solubility and oral activity.

Also included in this invention are O-lower alkanoyl esters of the compounds of Formula I having from 2-8 carbon atoms in each alkanoyl group such as acetyl, isobutyryl, propionyl, isovaleryl, n-heptanoyl and others. The triester derivatives are exemplified but one or more hydroxy can be esterified stepwise, using synthetic methods known to the art. The ester derivatives are prepared by treating the trihydroxy parent of Formula I with either a stoichiometric amount or an excess of an acid bromide or anhydride in the presence of an organic base optionally in an organic solvent.

It will be obvious to one skilled in the art that the compounds of Formula I may be present as diastereoisomers which may be resolved into d, l optical isomers. Resolution of the optical isomers may be conveniently accomplished by fractional crystallization of their salts with optically active acids from appropriate solvents. Specific methods of resolution are disclosed in Swiss patent 555,831. Unless otherwise specified herein or in the claims, it is intended to include all isomers, whether separated or mixtures thereof. Where isomers are separated, the desired pharmacological activity will usually predominate in one of the isomers however usually the mixture of isomers is used for the purpose of this invention.

The compounds of Formula I are prepared by N-allylation of a compound of the formula:

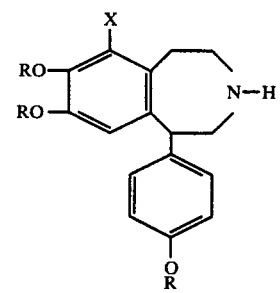

II in which X is halo and each R is a lower alkyl, especially methyl, benzyl or, when two are taken together in the benz-ring, methylene or ethylene. The N-allylation most conveniently is carried out using allyl bromide, chloride or iodide in an inert organic solvent especially acetonitrile in the presence of a tertiary organic base such as pyridine, triethylamine or dimethylaniline.

The protective R groups are then removed by ether cleavage agents which are known to the art such as boron tribromide of 48% hydrogen bromide to give the desired compounds of Formula I.

The intermediates of Formula II are generally prepared from precursors of the following formula:

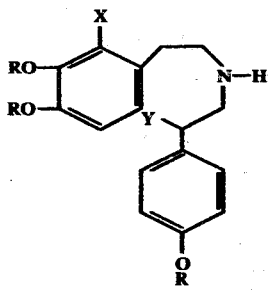

III in which Y is hydroxyl or its functional equivalent, X and R are as defined above, by means of an intramolecular cyclization effected by reaction with a cyclizing agent such as a strong acid for example, trifluoroacetic acid, polyphosphoric acid, sulfuric acid, the preferred sulfuric acid in trifluoroacetic acid, polyphosphoric ester, methanesulfonic acid in methylene chloride or hydrobromic acid as well as a Lewis acid such as boron trifluoride, aluminum chloride or stannic chloride which is able to generate the desired carbonium ion from the substituent X.

The intermediates of Formula III above are conveniently prepared by heating equimolar amounts of a styrene oxide with a 3,4-dialkoxy-2-halophenethylamine or by reaction of such a phenethylamine with a blocked bromohydrin as disclosed specifically in the examples.

The alternative and preferred blocked bromohydrin method comprises condensing a 2-halo-3,4-lower alkoxyphenethylamine with an O-protected α-phenylbromohydrin. The O-protecting group may be ay of those known to be useful in the art for this general purpose but the isobutyl is preferred. The reaction is most conveniently run in a suitable solvent such as dimethylformamide or dimethylacetamide in the presence of base such as carbonate. Temperatures may run from 75° up to about 125°. The mole ratio is 1 to 1. The O-protective group is then split as known to the art. Details of this method are in the Examples.

The phenethylamines which are used as starting materials for this method are either known or are prepared by methods described in U.S. Pat. Nos. 3,211,792, 3,804,839, 3,869,474, Chem. Abst. 80, 95398, J. Am. Chem. Soc. 78 4419 (1956).

Biological Spectrum of the Compounds

The compounds of Formula I have been unexpectedly found to have a unique hemodynamic profile that is characterized by reduced arterial blood pressure, reduced cardiac rate and reduced myocardial work with an augmented heart stroke volume and increased renal perfusion.

The compounds therefore are especially useful as anti-anginal agents. For a discussion of the treatment and etiology of angina pectoris as well as extension of antianginal agents to other abnormal states see "Essentials of Pharmacology", J. A. Bevin, 1969 Harper & Row, page 284.

The spectrum of activity of these new compounds is demonstrated by three pharmacological procedures: (1) The normotensive anesthetized dog test protocol where mean arterial blood pressure (MAP), renal blood flow (RBF), renal vascular resistance (RVR) and heart rate (HR) are monitored after infusion in μg/Kg/min doses using the procedure described in General Pharmacology 8 1 (1977) for assaying peripheral dopaminergic effects especially on the kidney, (2) the turning rat anti-Parkinsonism test for central dopaminergic effects, Advances in Neurology 9 165 (1975) and (3) the spontaneously hypertensive rat.

The following data illustrates the desirable spectrum of activity of the compounds of this invention compared with that of related compounds whose structures are considered closer to those claimed than are the structures specifically disclosed in the prior art.

Test 1—normotensive anesthetized dog

| (A) 3-allyl-6-chloro-7,8-dihydroxy-1(4-hydroxyphenyl)-2,3,4,5-tetrahydro-1H-3-benzazepine hydrobromide | | | | | (B) 3-allyl-6-chloro-7,8-dihydroxy-1-phenyl-2,3,4,5-tetrahydro-1H-3-benzazepine hydrobromide hydrate | | | | |
|---|---|---|---|---|---|---|---|---|---|
| Dose | % Change | | | | Dose | % Change | | | |
| μg/Kg/min. | MAP | RBF | RVR | HR | μg/Kg/min | MAP | RBF | RVR | HR |
| 0.3 | −3.5 | +8.7* | −11.4* | 0 | 0.3 | −1.8 | +13.0* | −13.1 | +6.8* |
| 3 | −14.4* | +18.1* | −27.8* | +0.5 | 3 | −8.5* | +32.5* | −30.7* | +7.4* |
| 30 | −16.9* | +20.0* | −30.7* | −8.7* | 30 | −22.3* | +6.6* | −22.3* | −1.0 |
| | | | | | 300 | +3.4 | −12.5* | +18.3* | −13.5* |
| (C) 6-chloro-7,8-dihydroxy-3-methyl-1(4-hydroxyphenyl)-2,3,4,5-tetrahydro-1H-3-benzazepine hydrobromide | | | | | (D) 6-chloro-7,8-dihydroxy-1-(4-hydroxyphenyl)-2,3,4,5-tetrahydro-1H-3-benzazepine | | | | |
| Dose | % Change | | | | Dose | % Change | | | |
| μg/Kg/min. | MAP | RBF | RVR | HR | μg/Kg/min | MAP | RBF | RVR | HR |
| 3 | −3.3 | 0 | −3.0 | 0 | 3 | −6.7 | +29.4 | −26.2* | +6.7* |
| 30 | +4.5 | +7.1 | −2.4 | 0 | 30 | −6.8 | +18.7* | −21.1* | +14.2* |
| 300 | +11.1* | +17.4* | −5.1 | 0 | 300 | −18.3* | −9.8* | −10.4* | +18.2* |

The starred numbers are considered significant.

These data demonstrate that at 30 micrograms the prototype 6-chloro species of this invention (A) demonstrated renal dopaminergic effects with increased kidney blood flow, as well as lower arterial blood pressure and bradycardia. Compound B whose structure lacks the phenolic hydroxy demonstrates no bradycardia at 30 micrograms and at 300 micrograms demonstrates bradycardia but no renal dopaminergic activity. Compound (C) whose structure has a 3-methyl in place of the 3-allyl demonstrates no renal dopaminergic or bradycardic activity. Compound (D) whose structure lacks the N-allyl demonstrates increased heart rate at all doses. The latter is the expected reaction to general peripheral vasodilation.

Test 2—Rat rotation (i.p.)

| (A) | 10 mg/Kg | 647 ± 84 | (B) | RD$_{500}$ | 0.03 mg/Kg |
|---|---|---|---|---|---|
|  | 10 | 631 ± 152 |  |  |  |
|  | 2.0 | 297 ± 64 |  |  |  |
|  | Significant but weak activity. |  |  |  |  |
| (C) | 10 mg/Kg | 762 ± 253 | (D) | 10 mg/Kg | 14 ± 7 |
|  | weak activity |  |  | inactive |  |

Test 3—Spontaneously hypertensive rat

Protocol:

Adult male spontaneously hypertensive rats, weighing about 350–400 grams, are anesthetized with sodium pentobarbital (65 mg/Kg, i.p.). The trachea are cannulated and the rats allowed to respire spontaneously. Pulsatile arterial blood pressure is measured from a cannulated carotid artery using a transducer. Mean arterial blood pressure is calculated as diastolic blood pressure plus ⅓ pulse pressure. Cardiac rate is monitored by a cardiotachometer triggered by the systotic blood pressure pulse. Drug solutions are administered through a cannulated tail vein. Following surgery, approximately 10 minutes are allowed to elapse for equilibration. The test compounds are administered in 0.9% saline. The results are recorded as mcg/Kg of free base. Control tracings are taken and readings taken at 5–10 minute intervals with increasing doses from 1–1000 mcg/Kg.

Compound A of this invention decreased arterial blood pressure and cardiac rate in a dose-related manner over 1–1000 mcg/Kg (i.v.). At the same dose range dopamine produced prominent tachycardia and arterial hypertension. The bradycardia and hypotension demonstrated by Compound A were antagonized by a ganglionic blocker (hexamethonium) and a dopamine antagonist (metoclopromide). The prototype compound of this invention (A) at an intraduodenal dose of 10 mg/Kg in the anesthetized dog produced bradycardia and arterial hypotension of 30–45 minutes duration. At 5 mg/Kg orally in the normal dog no side effects were observed.

Compound B, the deshydroxy congener, also produced bradycardia and hypotension in the SH rat but did not have a specificity of action since it was a very powerful central dopaminergic agent.

Compound (C) at from 1–1000 mg/Kg (i.v.) exhibited only trivial blood pressure effects and decreased cardiac rate only at the highest dose tested (1000 mcg/Kg).

In addition to the tests outlined above detailed study of Compound A, the prototype species of this invention, in the anesthetized dog demonstrated a reduced peripheral resistance in the systemic vasculature, increased stroke volume of the heart despite slowing and possibly a decreased adrenergic tone to the heart and vasculature.

The pharmaceutical compositions of this invention having a unique antihypertensive activity and especially activity against angina pectoris are prepared in conventional dosage unit forms by incorporating a compound of Formula I, an isomer or a pharmaceutically acceptable acid addition salt or ester derivative thereof, with a nontoxic pharmaceutical carrier according to accepted procedures in a nontoxic amount sufficient to produce the desired pharmacodynamic activity in a subject, animal or human. Preferably the compositions will contain the active ingredient in an active but nontoxic amount selected from about 25 mg to about 500 mg preferably about 15–75 mg of active ingredient per dosage unit but this quantity depends on the relative potency of the basic compound, the specific biological activity desired, the route of administration, oral or parenteral, and the condition of the patient. The lead or preferred compound (A) of this invention especially as the methyl sulfonate salt has been found to have a good absorbability from the gastrointestinal tract so oral dosage forms are of prime importance here preferably selected from the dosage unit ranges given above. Intravenous or subcutaneous doses would be lower.

The pharmaceutical carrier employed may be, for example, either a solid or liquid. Exemplary of solid carriers are lactose, terra alba, sucrose, talc, gelatin, agar, pectin, acacia, magnesium stearate, stearic acid, and the like. Exemplary of liquid carriers are isotonic saline for parenteral use or syrup, peanut oil, olive oil, water and the like for soft gelatine capsules. Similarly the carrier or diluent may include any time delay material well known to the art, such as glyceryl monostearate or glyceryl distearate alone or with a wax. Such sustained release products as well as derivatives which may be gradually metabolized to the active parent can be employed to prolong the unique biological activity of the compounds of this invention.

A wide variety of pharmaceutical forms can be employed. Thus, if a solid carrier for oral administration is used the preparation can be tableted, placed in a hard gelatin capsule in powder, regular or sustained release pellet form, or in the form of a troche or lozenge. The amount of solid carrier will vary widely but preferably will be from about 25 mg to about 1 g. If a liquid carrier is used, the preparation will be in the form of a syrup, emulsion, soft gelatin capsule, sterile injectable liquid such as an ampul, or an aqueous or nonaqueous liquid suspension.

The pharmaceutical preparations are made following the conventional techniques of the pharmaceutical chemist involving mixing, granulating and compressing when necessary, or variously mixing and dissolving the ingredients as appropriate to give the desired end product.

The method of producing antihypertensive activity especially for treating or preventing angina in accordance with this invention comprises administering internally to a subject in need of such activity a compound of Formula I or a pharmaceutically acceptable acid addition salt thereof, usually combined with a pharmaceutical carrier, in a nontoxic amount sufficient to produce said activity as described above. The route of administration may be any route which effectively transports the active compound to the dopamine receptors which are to be stimulated such as orally or parenterally, the oral route being preferred. Advantageously, equal oral doses within the ranges given above will be administered several times, such as from two to five times a day, with the daily dosage regimen being selected from about 25 mg to about 1.0 g preferably 50–500 mg/kg for oral dosage units. When the method described above is carried out dopaminergic activity especially against angina pectoris is produced. For an average size human for the preferred species (II) a preferred oral dose to show antihypertensive activity would be selected from the range of from about 25–75 mg for each dosage unit adapted for oral administration to be administered from 2–5 times daily.

The following examples are designed solely to illustrate the preparation and use of the compounds of this invention. The temperatures are Centigrade. Other variations of these examples will be obvious to those skilled in the art.

EXAMPLE 1

A solution of 540 g (containing 500 g) of 4-methoxystyrene in 2 l. of methylene chloride was cooled to −10° and 521.2 g of bromine added dropwise keeping the temperature between −5° and −10°. The last drop caused an abrupt change in color and the addition of bromine was stopped. The solvent was immediately removed under vacuum keeping the bath temperature below 35° and feeding the reaction solution in slowly. When the methylene chloride was gone and the warm oil was mixed with 1600 ml (5.5 ml/g product) of hexane to dissolve the remaining product in the evaporation flask and the bulk of the product. This required warming the solution on a steam bath. Charcoal was added, the solution filtered and the resulting pale yellow solution chilled in an ice bath to give 637 g (58.2% based on styrene, 66% based on bromine uptake) of crystals, m.p. 74°–78°. The pure 1-(4-methoxyphenyl)-1,2-dibromoethane melts at 80°–81°.

About 100 ml of liquid was distilled from 600 ml of t-butyl alcohol. To the slightly cooled contents were added 15 g of anhydrous powdered magnesium sulfate. The suspension was stirred for 15 minutes and then 100 g of the dibromoethane added. The reaction was refluxed with stirring for 1.5 hours. About 200 ml of methylene chloride was added to the cooled reaction mixture and the solids were removed by filtration. The solids were washed thoroughly with methylene chloride; the washings were combined with the filtrate and concentrated to dryness at 60°. The residue was stirred with 500 ml of pentane and 500 ml of water and the layers separated. The organic layer was washed with 5% sodium bicarbonate, dried and concentrated under vacuum to give 91.7 g (94%) of a tan oil; 2-bromo-1-(t-butoxy)-1-(4-methoxyphenyl)ethane.

A mixture of freshly prepared, undistilled 2-chloro-3,4-dimethoxyphenethylamine (50 g, 0.232 moles), the bromo-ether (62.4 g, 0.232 moles), powdered anhydrous potassium carbonate (96.1 g, 0.696 moles) and 175 ml sieve-dried dimethyl formamide (3.5 ml/g amine) was stirred and heated to 110° C. for 2 hours, cooled to room temperature, then poured into 1 liter of water. The mixture was extracted with three 250 ml portions of ethyl acetate; the combined extracts are washed three times with 250 ml of saturated brine, dried and concentrated to 109.6 g of viscous tan oil; N-[2-t-butoxy-2-(4-methoxyphenyl)ethyl]-2-(2-chloro-3,4-dimethoxyphenyl)ethylamine.

The crude t-butyl ether above (109.6 g, 0.232 mole) was heated and stirred on a steam bath with 500 ml of 10% aqueous sulfuric acid for 1 hour. The reaction mixture was made basic with 40% sodium hydroxide with cooling giving a tan semi-solid. Product was extracted into 150 ml of methylene chloride, washed once with 200 ml of water and dried. Removal of the solvent gave a tan solid which was recrystallized from ethanol/petroleum ether (refrigerated); the solid was collected and washed with cold 1:1 ether/petroleum ether. Upon air-drying the solid weighed 45.2 g (53%), m.p. 116°–118°; N-[2-hydroxy-2-(4-methoxyphenyl)ethyl]-2-(2-chloro-3,4-dimethoxyphenyl)ethylamine.

The aminoalcohol (787 g, 2.151 mole) was dissolved in 5900 ml of trifluoroacetic acid (7.5 ml/g), cooled to ambient temperature, and 179 ml (0.227 ml/g of amine, 3.225 mole) of sulfuric acid added slowly with cooling. The cooling was stirred at 25° for 3.5 hours and then 793 g (9.67 mole) of anhydrous sodium acetate added which raised the reaction temperature to 60°. Most of the trifluoroacetic acid was vacuum distilled off keeping the pot temperature <55°. After standing overnight, water was added and the mixture made basic with 14 N ammonium hydroxide with cooling. The mixture was extracted twice with methylene chloride which was then dried and concentrated under vacuum to give a yellow solid. Recrystallization of this from 1900 ml of ethyl acetate gave a solid which was collected and washed with ether. Drying gave 517 g (69%) of crystalline, 6-chloro-7,8-dimethoxy-1-(4-methoxyphenyl)-2,3,4,5-tetrahydro-1H-3-benzazepine, m.p. 140°–142.5°.

The trimethoxy compound (3.47 g, 0.01 m) in 50 ml of acetonitrile was mixed with 2.8 ml (0.02 m) of triethylamine and 1.4 ml (0.011 m) of allyl bromide. The mixture was heated at 85°–95° for 2½ hours. The reaction mixture was evaporated. The residue was suspended in water and extracted twice with ethyl acetate. The organic extracts were washed with water, brine and evaporated to give 2.6 g (67.2%) of a yellow oil, 3-allyl-6-chloro-7,8-dimethoxy-1-(4-methoxyphenyl)-2,3,4,5-tetrahydro-1H-3-benzazepine.

This material (2.6 g, 0.0067 m) was dissolved in 55 ml of methylene chloride and cooled to −15° at which time 6.0 ml (0.064 m) of boron tribromide in 40 ml of methylene chloride was added slowly over ½ hour. The reaction mixture was stirred at room temperature for 3 hours, cooled and treated with an excess of methanol slowly and with cooling. The methanol was evaporated to give a foam. This was dissolved in a minimum amount of methanol and cooled. Some ethyl acetate was added to induce separation of 1.85 g (65%) of 3-allyl-6-chloro-7,8-dihydroxy-1-(4-hydroxyphenyl)-2,3,4,5-tetrahydro-1H-3-benzazepine hydrobromide, m.p. 195°–199° (dec.).

An aliquot of the hydrobromide in aqueous methanol is neutralized using sodium carbonate solution. The base (500 mg) is reacted with methane sulfonic acid in methanol to give the methylsulfonate salt.

Substituting a stoichiometric quantity of 2-fluoro-3,4-dimethoxyphenethylamine in the synthetic procedure described above gives 6-fluoro-7,8-dimethoxy-1-(4-methoxyphenyl)-2,3,4,5-tetrahydro-1H-3-benzazepine. N-allylation and hydrolysis with boron tribromide gives 3-allyl-6-fluoro-7,8-dihydroxy-1-(4-hydroxyphenyl)-2,3,4,5-tetrahydro-1H-3-benzazepine hydrobromide. Substituting the analogous bromo starting material in the method described herein gives 6-bromo-7,8-dimethoxy-1-(4-methoxyphenyl)-2,3,4,5-tetrahydro-1H-3-benzazepine. Then N-allylation and hydrolysis with boron tribromide gives 3-allyl-6-bromo-7,8-dihydroxy-1-(4-hydroxyphenyl)-2,3,4,5-tetrahydro-1H-3-benzazepinehydrobromide.

EXAMPLE 2

The 6-bromo-trimethoxybenzazepine intermediate from Example 1 (7.8 g, 0.018 m) in 300 ml of methylene chloride and excess trifluoroacetic acid anhydride was stirred for 2 hours. The solvent was evaporated, toluene added. The mixture was again stripped to give the 3-amide. A mixture of 25 ml of butyl lithium (2.6 M, 0.65 m) in 200 ml of ether was cooled to −78° and the 3-amide (8.7 g) added in 60 ml of toluene. After stirring for 15 minutes a mixture of 9.1 g of iodine (0.036 m) and 60 ml of ethyl ether was added. After stirring while warming up to room temperature, the mixture was reacted with 200 ml of 10% hydrochloric acid at 0°. The mixture was stirred. The solid collected was taken into methylene chloride/methanol, washed with brine, dried and evaporated to give 6-iodo-7,8-dimethoxy-1-(4-methoxyphenyl)-2,3,4,5-tetrahydro-1H-3-benzazepine hydrochloride, m.p. 237–239. N-Allylation using allyl iodide followed by demethylation as in Example 1 gives 3-allyl-7,8-dihydroxy-6-iodo-1-(4-hydroxyphenyl)-2,3,4,5-tetrahydro-1H-3-benzazepine hydrobromide.

EXAMPLE 3

3-Allyl-6-chloro-7,8-dihydroxy-1-(4-hydroxyphenyl)-2,3,4,5-tetrahydro-1H-3-benzazepine hydrobromide (1.0 g) is slurried in 200 ml of trifluoroacetic acid then 1.29 ml of acetyl bromide is added. The mixture is heated at reflux for 2 hours then stirred for 2 hours. After evaporation to dryness the residue is taken up in benzene and concentrated to give 3-allyl-6-chloro-7,8-diacetoxy-1-(4-acetoxyphenyl)-2,3,4,5-tetrahydro-1H-3-benzazepine hydrobromide.

Similarly the isobutyryloxy, propionyloxy, isovaleryloxy, n-butyryloxy, n-heptanoyloxy and other higher derivatives are prepared at the catecholic hydroxy groups or at all three hydroxy sites.

| Ingredients | Mg. per Capsule |
| --- | --- |
| 3-Allyl-6-chloro-7,8-dihydroxy-1-(4-hydroxyphenyl)-2,3,4,5-tetrahydro-1H-3-benzazepine hydrobromide | 50 (free base) |
| Magnesium stearate | 2 |
| Lactose | 150 |

The above ingredients are thoroughly mixed and placed into hard gelatin capsules. Such capsules are administered orally to subjects in need of treatment from 1–5 times daily to induce a specific dopaminergic activity to treat the symptoms of angina.

What is claimed is:

1. A compound of the structural formula:

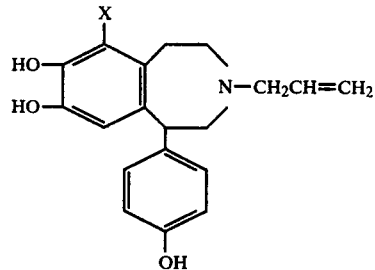

in which X is halo; together with a pharmaceutically acceptable acid addition salt or O-lower alkanoyl ester thereof.

2. The compound of claim 1 being 3-allyl-6-chloro-7,8-dihydroxy-1-(4-hydroxyphenyl)-2,3,4,5-tetrahydro-1H-3-benzazepine or a pharmaceutically acceptable acid addition salt thereof.

3. The compound of claim 1 being 3-allyl-6-iodo-7,8-dihydroxy-1-(4-hydroxyphenyl)-2,3,4,5-tetrahydro-1H-3-benzazepine or a pharmaceutically acceptable acid addition salt thereof.

4. The compound of claim 1 being 3-allyl-6-chloro-7,8-dihydroxy-1-(4-hydroxyphenyl)-2,3,4,5-tetrahydro-1H-3-benzazepine as the base.

5. The compound of claim 2 as the methanesulfonate, hydrochloride or hydrobromide salt.

6. The method of treating angina pectoris in a subject in need thereof comprising administering orally or by parenteral injection a nontoxic antianginally effective quantity of a compound of claims 1, 2, 3, 4 or 5.

7. The pharmaceutical composition having antianginal activity comprising a nontoxic anti-anginal quantity of a compound of claims 1, 2, 3, 4 or 5 combined with a pharmaceutical carrier.

* * * * *